United States Patent [19]

Henry et al.

[11] Patent Number: 5,908,867
[45] Date of Patent: Jun. 1, 1999

[54] REDUCTION OF HAIR GROWTH

[76] Inventors: James P. Henry, 10257 Meadow Fence Ct., Myersville, Md. 21773; Gurpreet S. Ahluwalia, 8632 Stableview Ct., Gaithersburg, Md. 20882; Edward Kaszynski, 12928 Dean Rd., Wheaton, Md. 20906; Douglas Shander, 16112 Howard Landing Dr., Gaithersburg, Md. 20878

[21] Appl. No.: 08/684,287

[22] Filed: Jul. 18, 1996

[51] Int. Cl.$^6$ .......................... A61K 31/11; A61K 31/70; A61K 38/00

[52] U.S. Cl. .............................. 514/693; 514/11; 514/25; 514/27; 514/255; 514/315; 514/422; 514/428; 514/666; 514/669; 514/629

[58] Field of Search ................................. 514/23, 25, 11, 514/693, 422, 666, 629, 299, 315, 428, 669, 27, 255

[56] References Cited

U.S. PATENT DOCUMENTS

| | | |
|---|---|---|
| 3,426,137 | 2/1969 | Philpitt et al. . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glea . |
| 4,269,831 | 5/1981 | Ferrari et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Brener et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,474,763 | 12/1995 | Shander et al. . |
| 5,532,227 | 7/1996 | Golub et al. . |

FOREIGN PATENT DOCUMENTS

| | | |
|---|---|---|
| 0 277 428 A2 | 8/1988 | European Pat. Off. . |
| 0 295 092 A2 | 12/1988 | European Pat. Off. . |
| 0 295 538 A2 | 12/1988 | European Pat. Off. . |
| 0 308 919 A1 | 3/1989 | European Pat. Off. . |
| 0413528A1 | 10/1990 | European Pat. Off. . |
| 0532219A2 | 2/1992 | European Pat. Off. . |
| 2632526 | 12/1989 | France . |
| 1 458 349 | 12/1976 | United Kingdom . |
| WO 93/13775 | 7/1993 | WIPO . |
| WO 93/14750 | 8/1993 | WIPO . |
| WO 96/26712 | 9/1996 | WIPO . |
| WO 97/15282 | 5/1997 | WIPO . |

OTHER PUBLICATIONS

Potter–Perigo et al., *Biochemistry and Biophysics*, "Altered Proteoglycan Synthesis via the False Acceptor Pathway Can Be Dissociated from B–D–Xyloside Inhibition of Proliferation," 297(1):101–109, (1992).

Butler, *Histochemical Journal*, "Glycosaminoglycans of Hair Follicles of Dog Skin," 7:67–75, (1975).

Elbein, *The FASEB Journal*, "Glycosidase Inhibitors: Inhibitors of N–linked Oligosaccharide Processing," 5:3055–3063, (1991).

Couchman, *The Journal of Investigative Dermatology*, "Hair Follicle Proteoglycans," 101(1):60S–64S (1993).

Harmon et al., *British Journal of Dermatology*, "Hair Fibre Production by Human Follicles in Whole–organ Culture," 415–423, (1994).

Li et al., *Proc. Natl. Acad. Sci. USA*, "Hair Shaft Elongation, Follicle Growth, and Spontaneous Regression in Long–term, Gerlatin Sponge—supported Histoculture of Human Scalp Skin," 89:8764–8768, (1992).

Adachi et al., *J. Soc. Cosmet. Chem.*, "Human Hair Follicles: Metabolism and Control Mechanisms," 21:901–924, (1970).

Philpott et al., *Journal of Dermatological Science*, "Human Hair Growth in vitro: A Model for the Study of Hair Follicle Biology," 7:S55–S72, (1994).

Elbein, *Ann. Rev. Biochem.*, "Inhibitors of the Biosynthesis and Processing of N–Linked Oligosaccharide Chains," 497–534, (1987).

Jindo et al., *The Journal of Dermatology*, "Organ Culture of Mouse Vibrissal Hair Follicles in Serum–free Medium," 20:756–762, (1993).

Hardingham et al., *The FASEB Journal*, "Proteoglycans: Many Forms and Many Functions," 6:861–870 (1992).

Li et al., *In Vitro Cell. Dev. Biol.*, "Skin Histoculture Assay for Studying the Hair Cycle," 28A:695–698, (1992).

Silbert, *The Journal of Investigative Dermatology*, "Structure and Metabolism of Proteoglycans and Glycosaminoglycans," 79(1):31s–37s, (1982).

Harmon et al., *SID Abstracts*, "12–O–Tetradecanoylphorbol–12–Acetate Inhibits Human Hair Follicle Growth and Hair Fiber Production in Whole–organ Cultures," 102:533 (1991).

Salzer et al., *Pharmacology Hear. Res.*, "Cochlear Damage and Increased Threshold in Alpha–difluoromethylornithine (DFMO) Treated Guinea Pigs," 45(1–2):101–102, (1990) Abstract.

Sato, *Biology and Disease of the Hair*, "The Hair Cycle and its Control Mechanism," 3–12, (1976).

(List continued on next page.)

*Primary Examiner*—Rebecca Cook
*Attorney, Agent, or Firm*—Fish & Richardson P.C.

[57] ABSTRACT

A method of reducing hair growth in a mammal includes applying, to an area of skin from which reduced hair growth is desired, a dermatologically acceptable composition containing a compound that inhibits the formation of glycoproteins, proteglycans, or glycosaminoglycans in an amount effective to cause a reduction in hair growth.

52 Claims, No Drawings

OTHER PUBLICATIONS

Goos et al., *Arch. Dermatol. Res.*, "An Improved Method for Evaluating Antiandrogens," 273:333–341, (1982).

Messenger, *The Society for Investigative Dermatology*, "The Control of Hair Growth: An Overview," 101(1):4S–9S, (1993).

Simpson et al., *British Journal of Dermatology*, "The Effect of Topically Applied Progesterone of Sebum Excretion Rate," 100:687–692, (1979).

Johnson et al., *Biochemistry*, "Inhibition of Hexokinase and Protein Kinase Activities of Tumor Cells by a Chloromethyl Ketone Derivative of Lactic Acid," 21(12):2984–2989, (1982).

Mackaua, J. Dermat. 6, 191–195, 1979.

Medline AN 91123748, Westgate et al, Feb. 1991.

Kosmet AN 8676, Taylor et al, 1992.

Kosmet AN 7833, Paus, 1991.

Embase Abstract No. 95229541. Schon et al, 1995.

Biosis abstract No. 96:333955, Csabayova et al, 1995.

ered from various parts of the body essentially for cosmetic reasons. For example, it is generally preferred to have hair on the scalp but not on the face.

REDUCTION OF HAIR GROWTH

BACKGROUND OF THE INVENTION

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Glycoproteins, proteoglycans, and glycosaminoglycans are three related components present in most mammalian tissues including skin and hair follicles.

Glycoproteins are protein molecules with oligosaccharide chains covalently attached to their polypeptide backbone structure. The oligosaccharide chains consist of sugar residues, which may include glucose, galactose, mannose, N-acetylgalactosamine, N-acetylglucosamine, fucose, arabinose, xylose, and sialic acids (example, N-acetylneuraminic acid). The oligosaccharides composed of these nine sugar residues are linked to the protein molecules with either O- or N-glycosidic linkage to form a glycoprotein molecule. The oligosaccharide chain is first synthesized on a lipid carrier, dolichol, and then transferred to the protein molecule to form a glycoprotein.

The synthesis of the oligosaccharide chain on dolichol is carried out in a specific manner in which the sequence of sugar residues is pre-determined by the regulatory enzymes involved in the synthesis. The first step in the synthesis is transfer of N-acetylglucosamine (GlcNAc) to dolichyl-phosphate to form GlcNAc-pyrophosphoryl-dolichyl (GlcNAc-P-P-Dol), which acts as an acceptor for an additional molecule of GlcNAc. Nine molecules of mannose (Man) and three molecules of glucose (Glc) are attached to this molecule to form $Glc_3Man_9(GlcNAc)_2$-PP-dolichol. The completed oligosaccharide chain $[Glc_3Man_9-(GlcNAc)_2]$ is then transferred to an acceptor protein catalyzed by an enzyme (oligosaccharide transferase). The oligosaccharide chain on this glycoprotein is further modified by enzymes such as glycosidases to form an active glycoprotein.

It is known that the process of glycoprotein formation (or protein glycosylation) can be inhibited at several steps by using select inhibitors.

For example, the synthesis of N-acetyl-glucosamine-pyrophosphoryl-dolichyl (GlcNAc-P-P-Dol), the first step in lipid linked oligosaccharide formation, is inhibited by antibiotics such as bacitracin, tunicamycin, amphomycin, tsushimycin, diumycin, showdomycin, amphortericine, streptovirudin, and mycospocidin. In addition, the formation of $(Glc_3Man_9-GlcNAc)_2$-PP-dolichol and the protein glycosylation step of transferring the core oligosaccharide chain to the acceptor protein molecule is inhibited by sugar analogs such as 2-deoxy-2-fluoro-mannose, fucose, mannose, D-glucasoamine, N-acetyl-D-glucasomine, and galactose. Also, the modification of the oligosaccharide chain of glycoprotein to form the active glycoprotein is inhibited by inhibitors of glucosidase I and II (e.g., castanospermine, deoxynojirimycin, and methyldeoxynojirimycin), inhibitors of mannosidase I (e.g., deoxymannojirimycin), inhibitors of mannosidase II (e.g., swainsonine). Other inhibitors of the processing include 2,5-dihydroxymethyl-3,4-dihydropyrrolidine, and 1,4-dideoxy-1,4-iminomannitol.

Proteoglycans, like glycoproteins, consist of a core protein molecule covalently attached to glycosaminoglycan (polysaccharide) chain(s). The distinction between proteoglycans and glycoproteins is based on the chemical nature and the arrangement of sugar residues of the attached polysaccharides. Glycosaminoglycan consists of linear polysaccharide chains made of a repeating sequence of an aminosugar hexosamine (D-glucosamine or D-galactosamine) and uronic acid (D-glucuronic acid or L-iduronic acid) residues. At least seven different types of glycosaminoglycans have been identified. Each differs from the others by the nature and/or arrangement of the sugar moieties and the degree of sulfation. Glycosaminoglycans, except hyaluronic acid, typically are synthesized attached to the protein molecule (i.e., as proteoglycans). The chain elongation is initiated by either xylosylation of select serine residues of protein (the xylose-serine bond formed is unique to proteoglycans), or a bond between N-acetylhexosamine (GalNAc or GlcNAc) and either the serine or the asparagine residue of a protein. Additional sugar residues then are added, and are further modified by the introduction of sulfate groups.

The proteoglycans generally are referred to by simple names based on their localization and/or function, or by names based on the attached glycosaminoglycan chains. The common proteoglycans include aggrecan, decorin, syndecan 1, versican, BM-CSPG (basement membrane-chondroitin sulfate containing proteoglycan), perlecan (heparan sulfate proteoglycan), biglycan, and fibromodulin.

The common glycosaminoglycans include chondroitin sulfates, keratan sulfates, dermatan sulfate, heparan sulfate, heparin, and hyaluronic acid. With the exception of hyaluronic acid, which is found as a free polysaccharide, all other glycosaminoglycans typically exist as proteoglycans.

It is known that inhibitors of glycosaminoglycan and proteoglycan formation include xylosides such as nitrophenyl-β-xylopyranoside, nitrophenyl-N-acetyl-β-D-xalactosamide, 4-methylumbelliferyl-β-D-xyloside, and methyl-β-xylopyranoside. These act as artificial acceptors and compete with the core protein molecule for the synthesis of glycosaminoglycan chain, especially at the initial xylosylation step.

Additional compounds that are known to affect one or more steps in the synthesis of glycoproteins, glycosaminoglycans, and proteoglycans include an ionophore monensin, which inhibits the terminal glycosylation reaction; inhibitors of β-galactosidase like benzyl-N-acetyl-β-D-galactosamide, phenyl-N-acetyl-β-D-galactosamide, and nitrophenyl-N-acetyl-β-D-galactosamide; and compounds that affect exocytosis (release) of proteoglycans, like diethylcarbamazine.

SUMMARY OF THE INVENTION

It has now been found that unwanted mammalian (including human) hair growth—particularly androgen stimulated hair growth—can be reduced by applying to the skin a dermatologically acceptable composition including a compound that inhibits the formation of glycoproteins, proteoglycans, or glycosaminoglycans. The unwanted hair growth which is reduced may be normal hair growth, or hair growth that results from an abnormal or diseased condition.

Preferred inhibitors of the formation of glycoproteins include compounds that inhibit the synthesis of N-acetyl-glucosamine-pyrophosphoryl-dolichyl; compounds that inhibit the formation of $Glc_3Man_9$-$(GlcNAc)_2$-PP-dolichol; compounds that inhibit the transfer of $Glc_3Man_9$-$(GlcNAc)_2$ to an acceptor protein; and compounds that inhibit one or more of the glycoprotein processing enzymes.

Preferred inhibitors of proteoglycan synthesis include compounds that inhibit the synthesis of glycosaminoglycans like chondroitin sulfate, keratin sulfate, dermatan sulfate, heparan sulfate, and heparin; and compounds that inhibit the formation of aggrecan, decorin, syndecan 1, versican, BM-CSPG (basement membrane-chondroitin sulfate containing proteoglycan), and perlecan (heparan sulfate proteoglycan).

Compounds that inhibit the formation of the glycosaminoglycan hyaluronic acid also can be used.

Other features and advantages of the invention will be apparent from the description of the preferred embodiments thereof, and from the claims.

DESCRIPTION OF THE PREFERRED EMBODIMENTS

The hair growth reducing compound is incorporated in a non-toxic dermatologically acceptable topical composition which preferably includes a vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the hair growth inhibiting compound in the composition may be varied over a wide range up to a saturated solution, preferably from 0.1% to 30% by weight or even more; the reduction of hair growth increases as the amount of compound applied increases per unit area of skin. The maximum amount effectively applied is limited only by the rate at which the hair growth inhibiting compound penetrates the skin. Generally, the effective amounts range from 10 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm in major diameter, which grow thick black and coarse hair similar to human beard hair. These organs produce hair in response to androgens in the hamster. To evaluate the effectiveness of a composition including a hair growth reducing compound, the flank organs of each of a group of hamsters are depilated by applying a thioglycolate based chemical depilatory (Surgex); alternatively, hair were removed by shaving the flank organs prior to topical treatments. To one organ of each animal 10 μl of vehicle alone once a day is applied, while to the other organ of each animal an equal amount of vehicle containing a hair growth reducing compound is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 18%, more preferably at least about 40%, and most preferably at least about 60% when tested in the Golden Syrian hamster assay. A number of compositions were tested in the Golden Syrian hamster assay; the results are provided in the Table.

TABLE

| Compound | Dose | Vehicle | pH | Hair Mass (mg) ± SEM | | % Inhibition |
| --- | --- | --- | --- | --- | --- | --- |
| | | | | Treated | Control | |
| D(+)mannose | 30% | A | 6.0 | 0.61 ± .11 | 2.62 ± .19 | 77 ± 3 |
| L-(−)mannose | 30% | A | 6.5 | 0.76 ± .17 | 2.48 ± .24 | 71 ± 5 |
| 4-methylumbelliferyl-β-D-xyloside | 10% | C | 4.5 | 0.69 ± .11 | 2.29 ± .24 | 70 ± 4 |
| Diethylcarbamazine | 10% | A | 6.0 | 0.61 ± .06 | 2.20 ± .26 | 69 ± 5 |
| D-(+)fucose | 30% | A | 6.5 | 0.78 ± .09 | 2.44 ± .15 | 68 ± 4 |
| L-(−)fucose | 30% | A | 6.5 | 0.67 ± .07 | 2.03 ± .14 | 65 ± 5 |

TABLE-continued

| Compound | Dose | Vehicle | pH | Hair Mass (mg) ± SEM Treated | Control | % Inhibition |
|---|---|---|---|---|---|---|
| Nitrophenyl-N-β-xylopyranoside | 20% | C | 6.0 | 0.89 ± .12 | 2.13 ± .22 | 58 ± 5 |
| L-galactose | 15% | A | 8.0 | 0.92 ± .14 | 2.25 ± .20 | 59 ± 4 |
| D-(+)galactose | 15% | A | 9.0 | 0.97 ± .09 | 2.16 ± .23 | 57 ± 5 |
| Monensin | 10% | B |  | 0.87 ± .09 | 2.05 ± .19 | 56 ± 7 |
| N-acetyl-D-glucosamine | 15% | A | 9.0 | 1.30 ± .12 | 2.57 ± .07 | 48 ± 6 |
| Nitrophenyl-N-acetyl-β-D-Xalactosamide | 10% | C | 8.5 | 1.12 ± .10 | 2.12 ± .20 | 46 ± 4 |
| Bacitracin | 10% | A | 6.5 | 0.58 ± .10 | 1.20 ± .14 | 44 ± 12 |
| Benzyl-2-acetamido-2-deoxy-α-D-galactoproside | 10% | D | 7.0 | 1.39 ± .16 | 2.27 ± .25 | 38 ± 6 |
| Methyldeoxynojirimycine | 1% | A | 7.0 | 1.24 ± .56 | 1.64 ± .71 | 25 ± 11 |
| D-glucosamine | 10% | A | 6.0 | 1.20 ± .15 | 1.50 ± .16 | 21 ± 7 |
| Methyl-β-xylopyroanoside | 10% | E | 6.0 | 1.80 ± .28 | 2.30 ± .17 | 18 ± 11 |

Vehicle A: 68% Water, 16% ethanol, 5% propylene glycol, 5% dipropylene glycol, 4% benzyl alcohol, and 2% propylene carbonate.
Vehicle B: Ethanol 100%
Vehicle C: 80% Ethanol, 17.5% water, 2% propylene glycol dipelargonate (Emerest 2388), and 0.5% propylene glycol.
Vehicle D: 64% Ethanol, 18% propylene glycol, and 18% dimethyl sulfoxide.
Vehicle E: 90% vehicle C and 10% dimethyl sulfoxide.

It will be appreciated by those skilled in the art that the invention can be performed within a wide range of equivalent parameters of composition and conditions without departing from the spirit or scope of the invention or of any embodiment thereof.

We claim:

1. A method of reducing mammalian hair growth which comprises
   selecting an area of skin from which reduced hair growth is desired; and
   applying to said area of skin a dermatologically acceptable composition comprising a compound that inhibits the formation of a glycoprotein, a proteoglycan, and/or a glycosaminoglycan in an amount effective to cause a reduction in hair growth.

2. The method of claim 1, wherein said compound inhibits the formation of a glycoprotein.

3. The method of claim 1, wherein said compound inhibits the formation of a proteoglycan.

4. The method of claim 1, wherein said compound inhibits the formation of a glycosaminoglycan.

5. The method of claim 1, wherein said compound inhibits synthesis of N-acetyl glucosamine-pyrophosphoryl-dolichyl.

6. The method of claim 1, wherein said compound is selected from the group consisting of bacitracin, tunicamycin, amphomycin, tsushimycin, diumycin, showdomycin, amphortericine, streptovirudin, and mycospocidin.

7. The method of claim 1, wherein said compound inhibits formation of $Glc_3Man_9$-$(GlcNAc)_2$-PP-dolichol.

8. The method of claim 1, wherein said composition comprises 2-deoxy-2-fluoro mannose.

9. The method of claim 1, wherein said composition comprises fucose.

10. The method of claim 1, wherein said composition comprises mannose.

11. The method of claim 1, wherein said composition comprises D-glucasoamine.

12. The method of claim 1, wherein said composition comprises N-acetyl-D-glucasomine.

13. The method of claim 1, wherein said composition comprises galactose.

14. The method of claim 1, wherein said composition inhibits transfer of $Glc_3Man_9$-$(GlcNAc)_2$.

15. The method of claim 1, wherein said compound inhibits a glycoprotein processing enzyme.

16. The method of claim 15, wherein said compound inhibits glucosidase I.

17. The method of claim 15, wherein said compound inhibits glucosidase II.

18. The method of claim 15, wherein said compound inhibits mannosidase I.

19. The method of claim 15, wherein said compound inhibits mannosidase II.

20. The method of claim 1, wherein said composition comprises castanospermine.

21. The method of claim 1, wherein said composition comprises deoxynojirimycin.

22. The method of claim 1, wherein said composition comprises methyldeoxynojirimycin.

23. The method of claim 1, wherein said composition comprises deoxymannojirimycin.

24. The method of claim 1, wherein said composition comprises 2,5-dihydroxymethyl-3,4-dihydropyrroliline.

25. The method of claim 1, wherein said composition comprises 1,4-dideoxy-1,4-iminomannitol.

26. The method of claim 1, wherein said compound inhibits the synthesis of a chondroitin sulfate.

27. The method of claim 1, wherein said compound inhibits synthesis of a keratin sulfate.

28. The method of claim 1, wherein said compound inhibits synthesis of dermatan sulfate.

29. The method of claim 1, wherein said compound inhibits synthesis of heparan sulfate.

30. The method of claim 1, wherein said compound inhibits synthesis of heparin.

31. The method of claim 1, wherein said compound inhibits synthesis of hyaluronic acid.

32. The method of claim 1, wherein said composition comprises a xyloside.

33. The method of claim 1, wherein said composition comprises nitrophenyl-β-xylopyranoside.

34. The method of claim 1, wherein said composition comprises nitrophenyl-N-acetyl-β-D-xalactosamide.

35. The method of claim 1, wherein said composition comprises 4-methylumbelliferyl-β-D-xyloside.

36. The method of claim 1, wherein said composition comprises methyl-β-xylopyranoside.

37. The method of claim 1, wherein said composition comprises an ionophore monensin.

38. The method of claim 1, wherein said composition comprises an inhibitor of β-galactosidase.

39. The method of claim 1, wherein said composition comprises benzyl-N-acetyl-β-D-galactosamide.

40. The method of claim 1, wherein said composition comprises phenyl-N-acetyl-β-D-galactosamide.

41. The method of claim 1, wherein said composition comprises nitrophenyl-N-acetyl-β-D-galactosamide.

42. The method of claim 1, wherein said compound affects the exocytosis of proteoglycans.

43. The method of claim 1, wherein said composition comprises diethylcarbamiazine.

44. The method of claim 1, wherein the concentration of said compound in said composition is between 1% and 30% by weight.

45. The method of claim 1, wherein the composition provides a reduction in hair growth of at least 18% when tested in the Golden Syrian hamster assay.

46. The method of claim 1, wherein the composition provides a reduction in hair growth of at least 40% when tested in the Golden Syrian hamster assay.

47. The method of claim 1, wherein the composition provides a reduction in hair growth of at least 60% when tested in the Golden Syrian hamster assay.

48. The method of claim 1, wherein the compound is applied to the skin in an amount of from 10 to 3000 micrograms of said inhibitor per square centimeter of skin.

49. The method of claim 1, wherein said mammal is a human.

50. The method of claim 49, wherein said area of skin is on the face of the human.

51. The method of claim 49, wherein said human is a woman suffering from hirsutism.

52. The method of claim 1, wherein the hair growth comprises androgen-stimulated hair growth.

* * * * *